United States Patent [19]

McNulty et al.

[11] 4,147,528
[45] Apr. 3, 1979

[54] 6-OXOPYRIMIDINE PLANT GROWTH REGULATORS

[75] Inventors: Patrick J. McNulty, Wyndmoor; Harlow L. Warner, Hatboro, both of Pa.

[73] Assignee: Rohm and Haas Company, Philadelphia, Pa.

[21] Appl. No.: 825,898

[22] Filed: Aug. 19, 1977

Related U.S. Application Data

[63] Continuation-in-part of Ser. No. 353,873, Apr. 23, 1973, abandoned.

[51] Int. Cl.² ............................................. A01N 9/22
[52] U.S. Cl. ...................................... 71/92; 544/242; 544/225
[58] Field of Search .................. 71/92; 544/242, 225

[56] References Cited

U.S. PATENT DOCUMENTS

| | | | |
|---|---|---|---|
| 3,745,161 | 7/1973 | Shen et al. | 260/250 R |
| 3,823,135 | 7/1974 | Pilgrim et al. | 71/92 |
| 3,869,457 | 3/1975 | Lutz et al. | 71/92 |
| 3,981,715 | 9/1976 | Lutz et al. | 71/92 |

Primary Examiner—Nicholas S. Rizzo

[57] ABSTRACT

Compounds of the formula

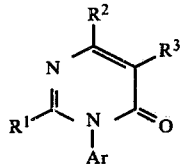

wherein
R¹ is hydrogen, alkyl, aryl, or aralkyl,
R² is alkyl, aryl, or aralkyl,
R³ is carboxy, carboxylate, carbalkoxy, cyano, carbamoyl, sulfo, sulfonate, alkoxysulfonyl, or sulfonamide, and
Ar is unsubstituted or substituted aryl,
are active as plant growth regulators, and particularly as chemical hybridization agents.

18 Claims, No Drawings

6-OXOPYRIMIDINE PLANT GROWTH REGULATORS

This is a continuation-in-part application of U.S. application Ser. No. 353,873 filed Apr. 23, 1973, now abandoned.

This invention relates to novel compounds which show activity as plant growth regulators, particularly as chemical hybridization agents, to growth regulant compositions which comprise these compounds, and to methods of regulating the growth of plants, particularly by inducing selective male sterility, with these compounds and compositions.

The cereal grains, such as corn, wheat, rice, rye, barley, millets, sorghum, and teff are among the major food crops throughout the world. This importance has led to extensive research to improve both the productivity and food value of these crops. One of the most important approaches taken to improve the quality and yield of the cereal grains has been hybridization. While hybridization has been an effective technique for some crops, most notably corn, there have been a number of problems with present techniques. For example, corn hybridization requires time-consuming hand detasseling or inefficient mechanical detasseling, possibly injuring the corn plant. Corn, barley, and wheat hybridization by means of cytoplasmic male sterile varieties can only be done with a limited genetic base, requiring a maintainer line and a restorer line. Furthermore, cytoplasmic male sterile techniques with barley and wheat necessitate a highly sophisticated approach to deal with the genetic complexities of these crops, and great success has not yet been achieved in developing a suitable approach. Since the induction of selective male sterility by chemical means would obviate many of the problems confronting the present hybridization techniques, new compounds which produce the desired sterility would be extremely desirable in dependably and economically supplying the male sterile plants needed for hybridization.

A new class of compounds has now been found which can be used to induce male sterility in cereal grains. The compounds of the invention are 6-oxopyrimidines (1,3-diazin-6-ones) having the formula

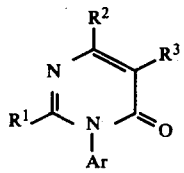

(I)

wherein $R^1$ is a hydrogen atom, an alkyl group, preferably having up to 4 carbon atoms, an aryl group, preferably having up to 10 carbon atoms, most preferably a phenyl or substituted phenyl group, or an aralkyl group, preferably having up to 10 carbon atoms, most preferably a benzyl or substituted benzyl group;

$R^2$ is an alkyl group, preferably having up to 4 carbon atoms, an aryl group, preferably having up to 10 carbon atoms, most preferably a phenyl or substituted phenyl group, or an aralkyl group, preferably having up to 10 carbon atoms, most preferably a benzyl or substituted benzyl group;

$R^3$ is a carboxy group (—COOH), a carboxylate group (—COO$^\ominus$), a carbalkoxy group (—COOR, wherein R is an alkyl group preferably having up to 12 carbon atoms), a carbamoyl group (—CONH$_2$), an alkyl or dialkyl carbamoyl group (—CONHR or —CONR$_2$), a cyano group (—CN), a sulfo group (—SO$_3$H), a sulfonate group (—SO$_3$—), an alkoxysulfonyl group (—SO$_3$R), or a sulfonamide group (—SO$_2$NH$_2$); and Ar is an unsubstituted aryl group, preferably having up to 10 carbon atoms, or a substituted aryl group, preferably having up to 10 carbon atoms in the aryl moiety, and up to three substituents having a total up to 6 carbon atoms.

In a preferred embodiment of the invention, $R^1$ is hydrogen, ($C_1$-$C_4$) alkyl, phenyl, chlorophenyl, methylphenyl, methoxyphenyl, nitrophenyl, dichlorophenyl, benzyl or chlorobenzyl;

$R^2$ is ($C_1$-$C_4$) alkyl, phenyl, chlorophenyl, methylphenyl, methoxyphenyl, nitrophenyl, dichlorophenyl, benzyl or chlorobenzyl;

$R^3$ is carboxy, carboxylate, carb ($C_1$-$C_{12}$) alkoxy, carbamoyl, ($C_1$-$C_4$) alkyl or di ($C_1$-$C_4$) alkyl, carbamoyl, cyano, sulfo, sulfonate, ($C_1$-$C_{12}$) alkoxysulfonyl or sulfonamide;

Ar is unsubstituted phenyl, α-naphthyl or β-naphthyl or phenyl, α-naphthyl or β-naphthyl substituted with one or more substituents selected from the group consisting of ($C_1$-$C_4$) alkyl, phenyl, ($C_1$-$C_4$) alkoxy, phenoxy, halo, nitro, trifluoromethyl, hydroxy, ($C_2$-$C_6$) alkoxyalkyl, ($C_2$-$C_6$) alkoxy, amino, ($C_1$-$C_4$) alkylamino, di ($C_1$-$C_4$) alkylamino, cyano, carboxy, carb ($C_1$-$C_4$) alkoxy, carbamoyl, ($C_1$-$C_4$) alkylcarbamoyl, di ($C_1$-$C_4$) alkylcarbamoyl, sulfo, sulfonamide, ($C_1$-$C_4$) alkylcarbonyl, carboxy ($C_1$-$C_4$) alkyl, ($C_1$-$C_4$) alkanoyloxy, halo ($C_1$-$C_4$) alkyl, ($C_1$-$C_4$) alkanoylamido, ($C_1$-$C_4$) alkylthio, ($C_1$-$C_4$) alkylsulfinyl, ($C_1$-$C_4$) alkylsulfonyl and the alkali metal, alkaline earth metal, transition metal or quaternary ammonium salts or ($C_1$-$C_{12}$) alkyl esters thereof.

Among the groups which $R^1$ can represent are hydrogen, methyl, ethyl, propyl, butyl, and higher alkyl groups, phenyl, chlorophenyl, methylphenyl, methoxyphenyl, nitrophenyl, dichlorophenyl, benzyl, chlorobenzyl, and the like. Among the groups which $R^2$ can represent are methyl, ethyl, propyl, butyl, and higher alkyl groups, phenyl, chlorophenyl, methylphenyl, methoxyphenyl, nitrophenyl, dichlorophenyl, benzyl, chlorobenzyl, and the like.

When $R^3$ is a carboxylate or a sulfonate group, any of the alkali metals, alkaline earth metals, or transition metals, or quaternary amines, can provide the cation. Representative cations include sodium, potassium, calcium magnesium, copper(II), zinc, ammonium, tetramethylammonium, and the like.

Among the groups which Ar can represent are unsubstituted aryl groups such as phenyl, α-naphthyl, β-naphthyl, and the like, as well as such aryl groups substituted with one or more alkyl groups, preferably having up to 4 carbon atoms, aryl groups, preferably phenyl or substituted phenyl groups, alkoxy groups, preferably having up to 4 carbon atoms, aryloxy groups, preferably phenoxy or substituted phenoxy groups, halogen atoms, such as fluoro, chloro, bromo, and iodo atoms, nitro groups, perhaloalkyl groups, such as trifluoromethyl groups, hydroxy groups, alkoxyalkyl groups, preferably having up to 6 carbon atoms, alkoxyalkoxy groups, preferably having up to 6 carbon atoms, amino groups, alkyl or dialkyl amino groups, preferably having up to 4 carbon atoms in each alkyl substituent, cyano groups, carboxy groups, carbalkoxy groups, preferably having up to 4 carbon atoms in the alkoxy moiety, carbamoyl groups, alkyl or dialkyl carbamoyl groups, preferably having up to 4 carbon atoms in each alkyl substituent, sulfo groups, sulfonamide groups, alkylcarbonyl or carboxyalkyl groups, preferably having up to 4 carbon atoms in the alkyl moiety, alkanoyloxy groups, preferably having up to 4 carbon atoms, haloalkyl groups, alkanoylamido groups, preferably having up to 4 carbon atoms, alkylthio groups, preferably having up to 4 carbon atoms, alkylsulfinyl groups, preferably having up to 4 carbon atoms, alkylsulfonyl groups, preferably having up to 4 carbon atoms, and the like.

In a more preferred embodiment $R^1$ is hydrogen or methyl; $R^2$ is methyl; and Ar is unsubstituted phenyl or naphthyl or phenyl or naphthyl substituted with up to three substituents selected from the group consisting of ($C_1$-$C_4$) alkyl, ($C_1$-$C_4$) alkoxy, halo, nitro, trihalomethyl, hydroxy, ($C_2$-$C_6$) alkoxyalkyl, ($C_2$-$C_6$) alkoxyalkoxy, amino, ($C_1$-$C_4$) alkylamino, di ($C_1$-$C_4$) alkylamino, cyano, carboxy, carb ($C_1$-$C_4$) alkoxy, carbamoyl, sulfo, sulfonamide, ($C_1$-$C_4$) alkylcarbonyl, ($C_1$-$C_4$) alkanoyloxy, halo, ($C_1$-$C_4$) alkyl, ($C_1$-$C_4$) alkylthio, ($C_1$-$C_4$) alkylsulfinyl, ($C_1$-$C_4$) alkylsulfonyl, phenyl and phenoxy.

Typical compounds within the scope of this invention include:
ethyl 1-(4-chlorophenyl)-1,6-dihydro-4-methyl-6-oxopyrimidine-5-carboxylate,
sodium 1-(4-chlorophenyl)-1,6-dihydro-4-methyl-6-oxopyrimidine-5-carboxylate,
1-(4-chlorophenyl)-1,6-dihydro-4-methyl-6-oxopyrimidine-5-carboxylic acid,
1,6-dihydro-2,4-dimethyl-6-oxo-1-phenylpyrimidine-5-carboxylic acid,
ammonium 1,6-dihydro-1-(4-methoxyphenyl)-4-methyl-6-oxopyrimidine-5-carboxylate
sodium 1-(4-acetoxyphenyl)-4-benzyl-2-ethyl-1,6-dihydro-6-oxopyrimidine-5-carboxylate,
potassium 1,6-dihydro-4-methyl-1-(4-nitrophenyl)-6-oxopyrimidine-5-carboxylate,
1-(3-bromophenyl)-1,6-dihydro-4-methyl-6-oxopyrimidine-5-carbonitrile,
1-(3,4-dichlorophenyl)-1,6-dihydro-4-methyl-6-oxopyrimidine-5-carboxamide,
cupric 1,6-dihydro-2,4-dimethyl-1-(4-nitrophenyl)-6-oxopyrimidine-5-carboxylate,
1-(4-cyanophenyl)-4-ethyl-1,6-dihydro-6-oxopyrimidine-5-carboxylic acid,
1,6-dihydro-4-methyl-6-oxo-1-p-tolylpyrimidine-5-sulfonic acid,
1-(3-chlorophenyl)-1,6-dihydro-4-methyl-6-oxo-2-phenylpyrimidine-5-carboxylic acid,
1-(4-carboxyphenyl)-1,6-dihydro-4-methyl-6-oxopyrimidine-5-carboxylic acid,
1,6-dihydro-2-methyl-6-oxo-1,4-diphenylpyrimidine-5-carboxylic acid,
sodium 1,6-dihydro-4-methyl-1-naphthyl-6-oxopyrimidine-5-carboxylate,
2-benzyl-1-(4-chlorophenyl)-1,6-dihydro-4-methyl-6-oxopyrimidine-5-carboxylic acid,
sodium 1-(2,4-dibromophenyl)-1,6-dihydro-2,4-dimethyl-6-oxopyrimidine-5-sulfonate,
decyl 1-(4-carbethoxyphenyl)-1,6-dihydro-4-methyl-6-oxopyrimidine-5-carboxylate,
and the like.

The compounds of the invention can be prepared by reacting a compound of the formula

$$R^2C(NH_2)=CHR^4 \quad \text{(II)}$$

wherein $R^2$ is as defined above and $R^4$ is a carbalkoxy group, a cyano group, or an alkoxysulfonyl group with an isocyanate of the formula

$$Ar-NCO \quad \text{(III)}$$

wherein Ar is as defined above. This reaction is generally carried out in a polar solvent, such as dimethylformamide, hexamethylphosphoric triamide, or the like, at a temperature of about 0 to about 100, and preferably about 25° to about 65° C., using stoichometric amounts of the reagents. Nonpolar solvents, such as toluene, xylene, and the like, can also be used but reaction with the isocyanate is less specific under these conditions. The product can be isolated by any convenient technique. However, under some reaction conditions, as described below, no isolation of this product is necessary prior to the cyclization reaction.

The compounds of Formula II are known compounds or can be made by known conventional methods. Those compounds wherein $R^4$ is a carbalkoxy group can be made by reacting an ester of a β-keto acid with ammonia (see, for example, Reppel et al., Arch. Pharm. 298, 342 (1965)) or by reacting an aryl or alkyl magnesium halide with an ester of an α-cyano acid (see, for example, Lukes et al., Collect. Czech. Chem. Commun., 25, 607 (1960)). Compounds of formula II wherein $R^4$ is a alkoxysulfonyl group can be made using similar conventional techniques. Compounds of Formula II wherein $R^4$ is a cyano group can generally be prepared by dimerizing acetonitriles. The isocyanates used in preparing the compounds of Formula III are also known compounds, which generally can be prepared from the corresponding amines by well-known phosgenation techniques. The products from the reaction between the compounds of Formula II and Formula III has the formula:

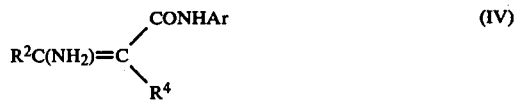

These compounds are cyclized to form pyrimidinones of the formula

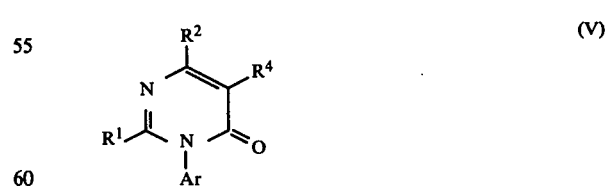

wherein $R^1$, $R^2$, $R^4$, and Ar are as defined above. The cyclization can be effected in several ways. First, compounds of Formula IV can be reacted with a 1,1,1-trialkoxyalkane or aralkane, such as triethyl orthoformate, triethyl orthoacetate, triethyl orthobenzoate, or the like. This cyclization reaction is generally carried out in acetic anhydride, without additional solvent at a temperature of about 25 to about 130, and preferably about 90° to about 120° C. Generally, about 1½ to 2 moles of acetic anhydride and about 2 to 4 moles of the trialkoxyalkane are used for each mole of the compound of Formula IV in the cyclization reaction.

The second cyclization technique is useful for preparing compounds of Formula V in which $R^1$ is a hydrogen atom. Compounds of Formula IV are treated with one equivalent or a slight excess of the dimethyl or diethyl acetal of dimethyl formamide in an aprotic solvent such as glyme (ethylene glycol dimethyl ether), tetrahydrofuran, dimethylformamide, diglyme, or the like, at a temperature of about 0 to about 100, and preferably about 25° to about 35° C.

In the third cyclization technique for preparing compounds of Formula V, compounds of Formula IV are reacted with one equivalent of Vilsmeier reagent, prepared by reacting dimethylformamide with one equivalent of $POCl_3$. Thus, when the isocyanation reaction is carried out in dimethylformamide as a solvent, no isolation of the product need be made since the Vilsmeier reagent can be generated in situ. This cyclization reaction is conveniently carried out at ambient temperature.

Further derivatives of the compounds of Formula V can be prepared by conventional techniques. For example, when $R^4$ represents a carbalkoxy group or an alkoxysulfonyl group, the free carboxylic or sulfonic acid can be prepared by conventional acid-catalyzed saponification, and the salts of these acids prepared by neutralization of the acids with an appropriate base, such as sodium hydroxide, potassium hydroxide, sodium hydride and the like, in a solvent such as glyme, potassium hydroxide, ammonium hydroxide, or the like, or by a salt exchange reaction. When $R^4$ represents a cyano group, the carbamoyl derivative can be conveniently prepared by partial hydrolysis of the cyano group, under acidic conditions. Other derivatives can be made by similar conventional techniques.

The following examples will further illustrate the compounds of the invention and their preparation, but are not intended to limit the invention in any way. Specific illustrative preparations of the compounds of Examples 1, 2, 3, 4, 9, 18, 25, 45, and 48 are provided. Table I lists typical compounds of the invention and Table II lists their melting points and elemental analyses.

EXAMPLE 1

Preparation of Ethyl 1-(4-Chlorophenyl)-1,6-dihydro-4-methyl-6-oxopyrimidine-5-carboxylate (a) Ethyl 3-Amino-2-(4-chlorophenylcarbamoyl)crotonate To a stirred solution of 12.9 g (0.10 mole) of ethyl 3-aminocrotonate in 50 ml of anhydrous dimethylformamide is added during 10 min. 15.36 g (0.10 mole) of p-chlorophenyl isocyanate in 50 ml of the same solvent. A mild exotherm (5° C.) results. After stirring for 3 hours, the reaction solution is slowly added with stirring to 1.5 l of deionized water. The white solid product is collected by vacuum filtration, washed with water and air dried at 45°–55° to give 23 g of ethyl 3-amino-2-(4-chlorophenylcarbamoyl)crotonate. Recrystallization of a 2.0 g. portion of this material from 15 ml of ethanol gives 1.5 g of pure ethyl 3-amino-2-(4-chlorophenylcarbamoyl)crotonate.

(b) Ethyl 1-(4-Chlorophenyl)-1,6-dihydro-4-methyl-6-oxopyrimidine-5-carboxylate

Method A

To a 2-l. three-necked flask are charged 250 g (0.88 mole) of ethyl 3-amino-2-(4-chlorophenylcarbamoyl)crotonate, 523 g. (3.54 moles) of triethyl orthoformate and 135 g (1.32 moles) of acetic anhydride. While stirring, reflux is initiated causing all solid to dissolve. After 15 to 16 hours at reflux, lower boiling liquid is distilled off (up to a head temperature of 90°–95° C.) and the dark reaction solution is subjected to rotary evaporation. Addition of the viscous residue to 4 l. of hot hexane with continued heating and agitation effects solidification. There is obtained 225 g (87%) of ethyl 1-(4-chlorophenyl)-1,6-dihydro-4-methyl-6-oxopyrimidine-5-carboxylate as a brown solid, m.p. 98°–100° C.

Method B

After the isocyanation reaction mixture as described in Example 1a has stirred for 3 hours, 15.3 g (0.10 mole) of phosphorus oxychloride is added during 10 min. (exotherm to 46° C.). The dark reaction slurry is stirred overnight, diluted with an additional 30 ml of dimethylformamide and 3.0 g of phosphorus oxychloride and stirred for three additional hours. The reaction solution is added to 3 l. of water, neutralized by the addition of sodium bicarbonate and the whole extracted with three 100 ml portions of methylene chloride. The organic phase is continuously extracted with water for 20 hours, filtered and evaporated. Crystallization of the dark residual syrup was accomplished by treatment with boiling hexane. There is obtained 21.1g (72% yield) of ethyl 1-(4-chlorophenyl)-1,6-dihydro-4-methyl-6-oxopyrimidine-5-carboxylate, m.p. 95°–102° C.

EXAMPLE 2

Preparation of 1-(4-Chlorophenyl)-1,6-dihydro-4-methyl-6-oxopyrimidine-5-carboxylic Acid Sulfuric acid (1 l.) is carefully diluted with 100 g of water (introduced as ice). To this solution is added 190 g (0.65 mole) of ethyl 1-(4-chlorophenyl)-1,6-dihydro-4-methyl-6-oxopyrimidine-5-carboxylate and the mixture is heated on a steam bath (pot temperature about 90°–95° C.) with stirring for 2.25 hours. After cooling, the dark reaction solution is poured into 10 l. of ice water and the precipitated product is isolated by vacuum filtration. Drying (40°–50° in air) gives 134 g (77.5%) of 1-(4-chlorophenyl)-1,6-dihydro-4-methyl-6-oxopyrimidine-5-carboxylic acid as a brown solid, m.p. 181°–3° C. dec.

EXAMPLE 3

Preparation of Sodium 1-(4-Chlorophenyl)-1,6-dihydro-4-methyl-6-oxopyrimidine-5-carboxylate To 5 ml of 1.0 N aqueous sodium hydroxide solution (5.0 mmoles) diluted with 50 ml of methanol is added one equivalent of 1-(4-chlorophenyl)-1,6-dihydro-4-methyl-6-oxopyrimidine-5-carboxylic acid prepared as in Example 2. After stirring for a short time the resulting slurry (pH 7–8) is evaporated in vacuo. The solid residue is slurried in ether and isolated by vacuum filtration. Drying gives a quantitative yield of sodium 1-(4-chlorophenyl)-1,6-dihydro-4-methyl-6-oxopyrimidine-5-carboxylate, m.p. >250° C.

EXAMPLE 4

Preparation of Ammonium
1-(4-Chlorophenyl)-1,6-dihydro-4-methyl-6-oxopyrimidine-5-carboxylate To 5 ml of ammonium hydroxide solution (28.7% assay) diluted with 50 ml of deionized water is added with stirring 1.33 g. (5.03 mmole) of 1-(4-chlorophenyl)-1,6-dihydro-2-methyl-6-oxopyrimidine-5-carboxylic acid. After 15 minutes at ambient temperature, the mixture is filtered to remove a small amount of insoluble matter and the clear filtrate is evaporated in vacuo. The solid residue is slurred twice in 50 ml of methanol and the latter removed. The resulting solid is isolated by filtration from an ether slurry and dried to give 1.1 g (75% yield) of ammonium 1-(4-chlorophenyl)-1,6-dihydro-4-methyl-6-oxopyrimidine-5-carboxylate, m.p. 200°–203° C. dec.

EXAMPLE 9

Preparation of Sodium
1,6-Dihydro-4-methyl-6-oxo-1-(4-tolyl)pyrimidine-5-carboxylate A mixture of 8.0 g (0.033 mole) of 1,6-dihydro-4-methyl-6-oxo-1-(4-tolyl)pyrimidine-5-carboxylic acid, prepared from ethyl 1,6-dihydro-4-methyl-6-oxo-1-(4-tolyl)pyrimidine-5-carboxylate by the hydrolysis method of Example 2, and one equivalent of sodium hydride (added as mineral oil dispersion), slurried in 300 ml of glyme is stirred at ambient temperature for 3 days. The solid product is isolated by filtration, slurried in ether and reisolated to give after drying 5.0 g (57% yield) of sodium 1,6-dihydro-4-methyl-6-oxo-1-(4-tolyl)pyrimidine-5-carboxylate, m.p. 208°–10° C. dec.

EXAMPLE 18

Preparation of Ethyl
1-(4-Chlorophenyl)-1,6-dihydro-2,4-dimethyl-6-oxopyrimidine-5-carboxylate This compound is prepared in 42% yield from ethyl 3-amino-2-(4-chlorophenylcarbamoyl)crotonate in a manner analogous to Example 1 substituting triethyl orthoacetate for triethyl orthoformate.

EXAMPLE 25

Preparation of Cupric
1-(4-Chlorophenyl)-1,6-dihydro-4-methyl-6-oxopyrimidine-5-carboxylate To a stirred solution of 2.86 g. (10mmole) of sodium 1-(4-chlorophenyl)-1,6-dihydro-4-methyl-6-oxopyrimidine-5-carboxylate, prepared as in Example 3, in 50 ml of deionized water is added a solution of 0.80 g. (5 mmole) of anhydrous cupric sulfate in 4 ml of DI water. After 15 minutes, the solid product is isolated by filtration and washed with water, ethanol and ether in that order. Drying gives 1.99 g. (67% yield) of cupric 1-(4-chlorophenyl)-1,6-dihydro-4-methyl-6-oxopyrimidine-5-carboxylate as a pale green solid, mp 198°–200° C. dec.

EXAMPLE 45

Preparation Ethyl
1-(4-Chlorophenyl)-4-ethyl-1,2-dihydro-6-oxopyrimidine-5-carboxylate A solution of 40.0 g (0.135 mole) of ethyl 3-amino-2-(4-chlorophenylcarbamoyl)-2-pentenoate (prepared from p-chlorophenyl isocyanate and ethyl 3-amino-2-pentenoate in a fashion analogous to Example 1(a) and 17.67 g (0.148 mole) of dimethylformamide dimethyl acetal in 400 ml of glyme is stirred for 3 days at ambient temperature, an additional 2.0 g of the acetal added and the whole stirred overnight. Solvent removal in vacuo followed by ether trituration gives 41 g of product as a soft yellow solid. Final purification is achieved by successive slurrying in 75 ml of fresh ether then hexane. There is obtained 30 g (73% yield) of ethyl 1-(4-chlorophenyl)-4-ethyl-1,2-dihydro-6-oxopyrimidine-5-carboxylate, m.p. 118°–20° C.

EXAMPLE 48

Preparation of
1-(4-Chlorophenyl)-1,6-dihydro-4-methyl-6-oxopyrimidine

Treatment of 2.93 g (10 mmole) of ethyl 1-(4-chlorophenyl)-1,6-dihydro-4-methyl-6-oxopyrimidine-5-carboxylate prepared as in Example 1 with either 20 ml of concentrated hydrochloric acid or a mixture of 10 ml of concentrated hydrochloric acid and 10 ml of acetic acid at reflux for 5 hours gives, after methylene chloride extraction and ethanol recrystallization, a 40–45% yield of 1-(4-chlorophenyl)-1,6-dihydro-4-methyl-6-oxopyrimidine, m.p. 177°–9° C.

TABLE I

6-OXOPYRIMIDINES

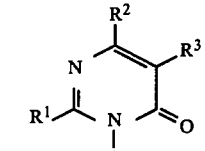

| Example No. | $R^1$ | $R^2$ | $R^3$ | Ar |
|---|---|---|---|---|
| 1 | H | $CH_3$ | $CO_2C_2H_5$ | 4-chlorophenyl |
| 2 | H | $CH_3$ | $CO_2H$ | 4-chlorophenyl |
| 3 | H | $CH_3$ | $CO_2Na$ | 4-chlorophenyl |
| 4 | H | $CH_3$ | $CO_2NH_4$ | 4-chlorophenyl |
| 5 | H | $CH_3$ | $CO_2H$ | phenyl |
| 6 | H | $CH_3$ | $CO_2Na$ | phenyl |
| 7 | H | $CH_3$ | $CO_2C_2H_5$ | 4-tolyl |
| 8 | H | $CH_3$ | $CO_2H$ | 4-tolyl |
| 9 | H | $CH_3$ | $CO_2Na$ | 4-tolyl |
| 10 | H | $CH_3$ | $CO_2C_2H_5$ | 4-nitrophenyl |
| 11 | H | $CH_3$ | $CO_2H$ | 4-nitrophenyl |
| 12 | H | $CH_3$ | $CO_2Na$ | 4-nitrophenyl |
| 13 | H | $CH_3$ | $CO_2H$ | 4-n-butylphenyl |
| 14 | H | $CH_3$ | $CO_2Na$ | 4-n-butylphenyl |
| 15 | H | $CH_3$ | $CO_2C_2H_5$ | 3,4-dichlorophenyl |
| 16 | H | $CH_3$ | $CO_2H$ | 3,4-dichlorophenyl |
| 17 | H | $CH_3$ | $CO_2Na$ | 3,4-dichlorophenyl |
| 18 | $CH_3$ | $CH_3$ | $CO_2C_2H_5$ | 4-chlorophenyl |
| 19 | $CH_3$ | $CH_3$ | $CO_2H$ | 4-chlorophenyl |
| 20 | $CH_3$ | $CH_3$ | $CO_2Na$ | 4-chlorophenyl |
| 21 | $CH_3$ | $CH_3$ | $CO_2H$ | 4-tolyl |
| 22 | $CH_3$ | $CH_3$ | $CO_2Na$ | 4-tolyl |
| 23 | H | $CH_3$ | $CO_2C_2H_5$ | phenyl |
| 24 | $CH_3$ | $CH_3$ | $CO_2C_2H_5$ | 4-tolyl |
| 25 | H | $CH_3$ | $CO_2Cu_{1/2}$ | 4-chlorophenyl |
| 26 | H | $CH_3$ | $CO_2C_2H_5$ | 4-bromophenyl |
| 27 | H | $CH_3$ | $CO_2H$ | 4-bromophenyl |
| 28 | H | $CH_3$ | $CO_2Na$ | 4-bromophenyl |
| 29 | H | $CH_3$ | $CO_2H$ | 1-naphthyl |
| 30 | H | $CH_3$ | $CO_2Na$ | 1-naphthyl |
| 31 | H | $CH_3$ | $CO_2C_2H_5$ | 4-methoxyphenyl |
| 32 | H | $CH_3$ | $CO_2H$ | 4-methoxyphenyl |
| 33 | H | $CH_3$ | $CO_2Na$ | 4-methoxyphenyl |
| 34 | H | $CH_3$ | $CO_2H$ | 2-chlorophenyl |
| 35 | H | $CH_3$ | $CO_2Na$ | 2-chlorophenyl |
| 36 | H | $CH_3$ | $CO_2H$ | 3-chlorophenyl |
| 37 | H | $CH_3$ | $CO_2Na$ | 3-chlorophenyl |
| 38 | H | $CH_3$ | $CO_2H$ | 4-chloro-2-tolyl |
| 39 | H | $CH_3$ | $CO_2Na$ | 4-chloro-2-tolyl |

TABLE I-continued
6-OXOPYRIMIDINES

Structure: 6-oxopyrimidine with substituents $R^1$, $R^2$, $R^3$, Ar

| Example No. | $R^1$ | $R^2$ | $R^3$ | Ar |
|---|---|---|---|---|
| 40 | H | $CH_3$ | $CO_2H$ | 4-chloro-3-tolyl |
| 41 | H | $CH_3$ | $CO_2Na$ | 4-chloro-3-tolyl |
| 42 | H | $CH_3$ | $CO_2C_2H_5$ | 2,6-xylyl |
| 43 | H | $CH_3$ | $CO_2H$ | 2,6-xylyl |
| 44 | H | $CH_3$ | $CO_2Na$ | 2,6-xylyl |
| 45 | H | $C_2H_5$ | $CO_2C_2H_5$ | 4-chlorophenyl |
| 46 | H | $C_2H_5$ | $CO_2H$ | 4-chlorophenyl |
| 47 | H | $C_2H_5$ | $CO_2Na$ | 4-chlorophenyl |
| 48 | H | $CH_3$ | H | 4-chlorophenyl |

TABLE II
Physical properties of 6-OXOPYRIMIDINES

| Example | MP (° C.) | | C | H | N | Cl |
|---|---|---|---|---|---|---|
| 1 | 105–7 | Theory | 57.45 | 4.48 | 9.57 | 12.11 |
|   |       | Found  | 57.44 | 4.31 | 9.50 | 12.28 |
| 2 | 183–4 | Theory | 54.46 | 3.43 | 10.58 | 13.40 |
|   |       | Found  | 54.33 | 3.63 | 10.40 | 13.50 |
| 3* | >250 | | | | | |
| 4* | 200–203 | | | | | |
| 5 | 181–3 | Theory | 62.60 | 4.39 | 12.16 | |
|   |       | Found  | 60.45 | 4.39 | 11.79 | |
| 6* | 223–5 | | | | | |
| 7 | 97–9 | Theory | 66.18 | 5.91 | 10.28 | |
|   |      | Found  | 66.44 | 6.10 | 10.33 | |
| 8 | 195–7 | Theory | 63.92 | 4.95 | 11.47 | |
|   |       | Found  | 63.97 | 4.95 | 11.45 | |
| 9* | 208–10 | | | | | |
| 10 | 143–5 | Theory | 55.14 | 4.32 | 13.85 | |
|    |       | Found  | 55.02 | 4.26 | 13.67 | |
| 11 | 189–90 | Theory | 52.36 | 3.30 | 15.26 | |
|    |        | Found  | 52.27 | 3.45 | 15.19 | |
| 12* | 103–5 | | | | | |
| 13 | 127–9 | Theory | 67.13 | 6.32 | 9.78 | |
|    |       | Found  | 67.02 | 6.32 | 9.78 | |
| 14* | 191–3 | | | | | |
| 15 | 89–91 | Theory | 51.39 | 3.70 | 8.56 | 21.67 |
|    |       | Found  | 51.39 | 3.84 | 8.34 | 21.37 |
| 16 | 185–8 | Theory | 48.18 | 2.71 | 9.36 | 23.70 |
|    |       | Found  | 47.70 | 2.57 | 9.03 | 23.42 |
| 17* | 243∝4 | | | | | |
| 18 | 129–30.5 | Theory | 58.73 | 4.92 | 9.13 | 11.57 |
|    |          | Found  | 59.07 | 5.06 | 9.16 | 11.70 |
| 19 | 248–9 | Theory | 56.01 | 3.98 | 10.05 | 12.74 |
|    |       | Found  | 56.10 | 4.20 | 10.02 | 12.93 |
| 20* | >250 | | | | | |
| 21 | 241–3 | Theory | 65.14 | 5.46 | 10.84 | |
|    |       | Found  | 65.26 | 5.53 | 10.62 | |
| 22* | >250 | | | | | |
| 23 | 70–2 | Theory | 65.11 | 5.46 | 10.84 | |
|    |      | Found  | 65.10 | 5.47 | 10.84 | |
| 24 | 75–6 | Theory | 67.12 | 6.33 | 9.78 | |
|    |      | Found  | 66.90 | 6.45 | 9.77 | |
| 25* | 198–200 | | | | | |
| 26 | 126–8 | Theory | 49.86 | 3.88 | 8.30 | +23.71 |
|    |       | Found  | 49.93 | 3.96 | 8.45 | 23.89 |
| 27 | 156–8 | Theory | 46.62 | 2.94 | 9.06 | +25.85 |
|    |       | Found  | 46.51 | 2.97 | 8.77 | 25.85 |
| 28* | 215 | | | | | |
| 29 | 184–6 | Theory | 68.57 | 4.32 | 9.90 | |
|    |       | Found  | 68.30 | 4.34 | 9.70 | |
| 30* | 210–17 | | | | | |
| 31 | 139–41 | Theory | 62.50 | 5.59 | 9.72 | |
|    |        | Found  | 62.53 | 5.61 | 9.67 | |
| 32 | 163–5 | Theory | 59.99 | 4.65 | 10.77 | |
|    |       | Found  | 59.89 | 4.71 | 10.63 | |
| 33* | 250–2 | | | | | |
| 34 | 176–8 | Theory | 54.45 | 3.43 | 10.59 | 13.40 |
|    |       | Found  | 54.48 | 3.43 | 10.98 | 13.54 |
| 35* | 208–10 | | | | | |
| 36 | 195–6 | Theory | 54.45 | 3.43 | 10.59 | 13.40 |
|    |       | Found  | 54.42 | 3.37 | 10.93 | 13.55 |
| 37* | 212–4 | | | | | |
| 38 | 219–20 | Theory | 56.02 | 3.98 | 10.05 | 12.74 |
|    |        | Found  | 55.93 | 3.96 | 10.00 | 12.99 |
| 39* | 233–4 | | | | | |
| 40 | 186–8 | Theory | 56.02 | 3.98 | 10.05 | 12.74 |
|    |       | Found  | 55.80 | 3.78 | 10.17 | 12.84 |
| 41* | 240–1 | | | | | |
| 45 | 118–20 | Theory | 58.73 | 4.92 | 9.13 | 11.57 |
|    |        | Found  | 58.53 | 4.98 | 9.35 | 12.55 |
| 46 | 165–7 | Theory | 56.01 | 3.98 | 10.05 | 12.72 |
|    |       | Found  | 55.95 | 3.95 | 10.30 | 13.34 |
| 47* | 227–9 | | | | | |
| 48 | 177–9 | Theory | 59.85 | 4.12 | 12.68 | 16.08 |
|    |       | Found  | 59.84 | 4.13 | 12.68 | 16.08 |

*No elemental analyses made of salts; identified and characterized by spectral data.
+Data for Br The compounds of the invention are useful for regulating plant growth. Typical plant responses include inhibition of growth, control of flowering, control of fruiting, inhibition of seed formation, and related growth regulatory responses. The compounds of the invention are particularly useful as chemical hybridization agents in cereal crops, such as wheat, barley, corn, rice, sorghum, millets, oats, rye, and the like. When used as chemical hybridization agents, the compounds effective induce selective male sterility, that is without also inducing significant female sterility, in the treated plants. As used herein, the term male sterility includes both actual male sterility, as evidenced by a lack of male flower parts or by sterile pollen, and functional male sterility, in which the male flower parts are unable to cause pollination.

When used as plant growth regulators, the compounds of the invention are applied in any amount which will be sufficient to effect the desired plant response without causing any undesirable or phytotoxic response. For example, when the compounds of the invention are used as chemical hybridization agents, they are generally applied to the crops to be treated at a rate of about 1/32 to about 20 pounds per acre and preferably about 1/16 to about 12 pounds per acre. The rate of application will vary depending on the crop being treated, the compound being used for treatment, and related factors. In rice, the preferred rate of application is about 1/16 to about 1 pound per acre. In wheat and barley, the preferred rate of application is about ½ to about 8 pounds per acre. In corn, the preferred rate of application is about 1½ to 12 pounds per acre.

To obtain hybrid seed, the following procedure is generally employed. The two parents to be crossed are planted in alternate strips. The female parent is treated with a compound of the invention. The male-sterile female parent thus produced will be pollinated by pollen from the other, male-fertile, male parent, and the seed produced by the female parent will be hybrid seed which can then be harvested by conventional means.

A preferred method of applying a compound of the invention as a chemical hybridization agent is by foliar application. When this method is employed, selective male sterility is most effectively induced when the compound is applied between flower initiation and meiosis. The compounds of the invention may also be applied as a seed treatment, by soaking the seed in a liquid formulation containing the active compound or by coating the seed with the compound. In seed treatment applications, the compounds of the invention will generally be applied at a rate of about 1 to about 50 ounces per hundred weight of seed. The compounds of the invention are also effective when applied to the soil or to the water surface in rice crops.

The compounds of the invention can be used as plant growth regulators either individually or in mixtures. They can also be used in combination with other plant growth regulators, such as auxins, giberellins, ethylene-releasing agents, such as ethephon, pyridones, cytokinins, and the like, and under some conditions may be used advantageously with other agricultural chemicals such as herbicides, fungicides, insecticides, and plant bactericides.

A compound of the invention can be applied to the growth medium or to plants to be treated either by itself or, as is generally done, as a component in a growth regulant composition or formulation which also comprises an agronomically acceptable carrier. By "agronomically acceptable carrier" is meant any substance which can be used to dissolve, disperse, or diffuse a compound in the composition without impairing the effectiveness of the compound and which by itself has no detrimental effect on the soil, equipment, crops, or agronomic environment. Mixtures of the compounds of the invention may also be used in any of these formulations. The compositions of the invention can be either solid or liquid formulations or solutions. For example, the compounds can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in foliar applications, to include adjuvants, such as wetting agents, spreading agents, dispersing agents, stickers, adhesives, and the like, in accordance with agricultural practices. Examples of adjuvants which are commonly used in the art can be found in the John W. McCutcheon, Inc. publication "Detergents and Emulsifiers Annual."

The compounds of the invention can be dissolved in any appropriate solvent. Examples of solvents which are useful in the practice of this invention include water, alcohols, ketones, aromatic hydrocarbons, halogenated hydrocarbons, dimethylformamide, dioxane, dimethyl sulfoxide, and the like. Mixtures of these solvents can also be used. The concentration of the solution can vary from about 2% to about 98% with a preferred range being about 20% to about 75%.

For the preparation of emulsifiable concentrates, the compound can be dissolved in organic solvents, such as benzene, toluene, xylene, methylated naphthalene, corn oil, pine oil, o-dichlorobenzene, isophorone, cyclohexanone, methyl oleate, and the like, or in mixtures of these solvents, together with an emulsifying agent which permits dispersion in water. Suitable emulsifiers include, for example, the ethylene oxide derivatives of alkylphenols or long-chain alcohols, mercaptans, carboxylic acids, and reactive amines and partially esterified polyhydric alcohols. Solvent-soluble sulfates or sulfonates, such as the alkaline earth salts or amine salts of alkylbenzenesulfonates and the fatty alcohol sodium sulfates, having surface-active properties can be used as emulsifiers either alone or in conjunction with an ethylene oxide reaction product. Flowable emulsion concentrates are formulated similarly to the emulsifiable concentrates and include, in addition to the above components, water and a stabilizing agent such as a water-soluble cellulose derivative or a water-soluble salt of a polyacrylic acid. The concentration of the active ingredient in emulsifiable concentrates of usually about 10% to 60% and in flowable emusion concentrates, this can be as high as about 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of about 20% to 98%, preferably about 40% to 75%. A dispersing agent may generally constitute about 0.5% to about 3% of the composition, and a wetting agent may generally constitute from about 0.1% to about 5% of the composition.

Dusts can be prepared by mixing the compounds of the invention with finely divided inert solids which may be organic or inorganic in nature. Materials useful for this purpose include, for example, botanical flours, silicas, silicates, carbonates and clays. One convenient method of preparing a dust is to dilute a wettable powder with a finely divided carrier. Dust concentrates containing about 20% to 80% of the active ingredient are commonly made and are subsequently diluted to about 1% to 10% use concentration.

Granular formulations can be prepared by impregnating a solid such as granular fuller's earth, vermiculite, ground corn cobs, seed hulls, including bran or othe grain-hulls, or similar material. A solution of one or more of the compounds in a volatile organic solvent can be sprayed or mixed with the granular solid and the solvent then removed by evaporation. The granular material can have any suitable size, with a preferable size range of 16 to 60 mesh. The active compound will usually comprise about 2 to 15% of the granular formulation.

The compounds of the invention can be applied as sprays by methods commonly employed, such as conventional hydraulic sprays, aerial sprays, and dusts. For low-volume applications a solution of the compound is usually used. The dilution and volume of application will usually depend upon such factors as the type of equipment employed, the method of application, the area to be treated and the type and stage of development of the weeds.

The following examples will further illustrate the growth regulatory activity of the compounds of the invention, but are not intended to limit the invention in any way.

EXAMPLE 49

Chemical Hybridization Activity

The following procedures are used to evaluate the activity of the compounds of the invention for inducing male sterility in cereals.

Spring wheat (*Triticum aestivium* var. Pictic) and spring barley (*Hordium vulgare* var. Dickson) are planted at a rate of 6 to 8 seeds in six-inch pots containing a non-sterile medium of two parts soil and one part humus. After emergence and at weakly intervals, the plants are fertilized with a water-soluble fertilizer (16-25-16) at a rate of 1 tsp./gal. of water and sprayed with malathion and benomyl for alphid and powdery mildew control respectively.

Test compounds are applied when the plants are in the initial stages of flag leaf elongation which usually occurs about 6 to 7 weeks after planting in wheat and 9 to 10 weeks after planting in barley. All test compounds are foliarly applied at rates of ½ and 5 lb/A on wheat and ½ and 3 lb/A on barley and in a 50 gal/A spray volume containing 2 oz/50 gal. of surfactant.

Immediately after spike emergence, each spike is covered with a glassine bag to prevent outcrossing, so that any seed set occurs is a result of self pollination. When the seeds of control spikes are mature, culm and spike length are measured and the seeds per spike are counted on all plants with bagged spikes.

Rice (*Oryza sativa* var. Belle Patna) is planted at a rate of five seeds in four-inch pots containing a sterile medium of two parts soil and one part humus. Three weeks after emergence, the plants are thinned to two plants per pot and the pots are placed in three inches of water to simulate paddy conditions. The plants are sprayed weekly with malathion for insect control and fertilized biweekly by placing a water-soluble high analysis fertilizer (16-25-16) supplemented with iron chelate directly into the paddy water at a rate of 1 tsp./gal. When flower development reaches the pre-boot stage (approx. 12 weeks after planting), test compounds are applied foliarly with a hand mist sprayer. Compounds are applied at rates of 1/128 and 1/16 lb/A in a carrier volume of 100 gal/A. with 4 oz/100 gal. of a surfactant. Approximately 8 weeks after treatment, when the seed matures, plant height is measured and seeds per spikes counted.

Percent sterility and percent height inhibition are calculated from the following formulas:

$$\% \text{ Sterility} = \frac{S_c - S_t}{S_c} \times 100$$

$S_c$ = seeds/bagged spike in untreated plants
$S_t$ = seeds/bagged spike in treated plants $$\% \text{ Height inhibition} = \frac{H_c - H_t}{H_c} \times 100$$

$H_c$ = height of untreated plants
$H_t$ = height of treated plants

Table III summarizes results obtained in the evaluation of compounds of the invention.

TABLE III
CHEMICAL HYBRIDIZATION ACTIVITY

| Compound of Example No. | Spring Wheat | | | Spring Barley | | |
|---|---|---|---|---|---|---|
| | Application Rate (lb./A) | Male Sterility (%) | Height Inhibition (%) | Application Rate (lb./A) | Male Sterility (%) | Height Inhibition (%) |
| 1 | 0.5 | 27 | 2 | | | |
|   | 5.0 | 67 | 13 | | | |
| 2 | 0.5 | 31 | 9 | | | |
|   | 5.0 | 87 | 12 | | | |
| 3 | 0.5 | 71 | 2 | 0.5 | 31 | 3 |
|   | 5.0 | 100 | 6 | 3.0 | 48 | 6 |
| 4 | 0.5 | 100 | | | | |
|   | 5.0 | 100 | | | | |
| 5 | 0.5 | 8 | 3 | | | |
|   | 5.0 | 16 | 3 | | | |
| 6 | 0.5 | 6 | 0 | 0.5 | 34 | 4 |
|   | 5.0 | 67 | 5 | 3.0 | 40 | 1 |
| 7 | 0.5 | 12 | 0 | 0.5 | 28 | 8 |
|   | 5.0 | 7 | 0 | 3.0 | 38 | 10 |
| 8 | 0.5 | 4 | 7 | 0.5 | 35 | 5 |
|   | 5.0 | 13 | 2 | 3.0 | 35 | 0 |
| 9 | 0.5 | 3 | 10 | 0.5 | 22 | 10 |
|   | 5.0 | 23 | 9 | 3.0 | 50 | 9 |
| 10 | 0.5 | 19 | 0 | 0.5 | 25 | 2 |
|    | 5.0 | 21 | 0 | 3.0 | 39 | 0 |
| 11 | 0.5 | 30 | 7 | 0.5 | 36 | 12 |
|    | 5.0 | 17 | 0 | 3.0 | 33 | 1 |
| 12 | 0.5 | 23 | 4 | 0.5 | 0 | 17 |
|    | 5.0 | 12 | 8 | 3.0 | 23 | 9 |
| 13 | 0.5 | | | | | |
|    | 5.0 | 23 | 0 | | | |
| 14 | 0.5 | | | | | |
|    | 5.0 | 5 | 1 | | | |
| 15 | 0.5 | 35 | 7 | 0.5 | | 18 |
|    | 5.0 | 36 | 16 | 3.0 | 96 | |
| 16 | 0.5 | 5 | 10 | 0.5 | 44 | 8 |
|    | 5.0 | 64 | 12 | 3.0 | 93 | 36 |
| 17 | 0.5 | 0 | 5 | 0.5 | 29 | 0 |
|    | 5.0 | 99 | 19 | 3.0 | 39 | 17 |
| 18 | 0.5 | 7 | 8 | | | |
|    | 5.0 | 29 | 20 | | | |
| 19 | 0.5 | 100 | | | | |
|    | 5.0 | 100 | | | | |
| 20 | 0.5 | 99 | 28 | 0.5 | 100 | 20 |
|    | 5.0 | 100 | 52 | 3.0 | 100 | 35 |
| 21 | 0.5 | 0 | 2 | | | |
|    | 5.0 | 36 | 17 | | | |
| 22 | 0.5 | 0 | 3 | | | |
|    | 5.0 | 41 | 19 | | | |
| 23 | 0.5 | | | 0.5 | 35 | 6 |
|    | 5.0 | 43 | 13 | 3.0 | 60 | 5 |

TABLE III-continued

CHEMICAL HYBRIDIZATION ACTIVITY

| | Spring Wheat | | | Spring Barley | | |
|---|---|---|---|---|---|---|
| Compound of Example No. | Application Rate (lb./A) | Male Sterility (%) | Height Inhibition (%) | Application Rate (lb./A) | Male Sterility (%) | Height Inhibition (%) |
| 24 | 0.5 | 7 | 14 | | | |
| | 5.0 | 6 | 2 | | | |
| | Rice | | | | | |
| 3 | 1/128 | 0 | 0 | | | |
| | 1/16 | 86 | 9 | | | |

EXAMPLE 50

Evaluation of Selective Male Sterility

Selective male sterility is demonstrated by treating spring wheat after spike initiation with a foliar application of test compounds at rates of 2, 4 and 6 lb/A. At anthesis, 6 treated spikes are covered with glassine bags to prevent outcrossing and 4 treated spikes are crossed with a male parent using the approach method of crossing. When seed are mature, the seed per spike are counted and plant height measured. Percent sterility and height inhibition are calculated according to the formulas noted above.

The percent hybrids is determined from the difference of the percent seed set in crossed spikes of treated plants and the percent seed set in covered spikes of treated plants.

Table IV summarizes typical results of these tests.

TABLE IV

SELECTIVE MALE STERILITY

| Example | Applic. Rate (lb/A) | Male Sterility (%) | Hybrids (%) | Height Inhibition (%) |
|---|---|---|---|---|
| 3 | 2 | 63 | 32 | 0 |
| | 4 | 96 | 95 | 6 |
| | 6 | 100 | 73 | 8 |

Useful selective male sterility is similarly obtained when corn (*Zea mays*) is treated with compounds of the invention.

The compounds of Examples 15 and 25 also show fungicidal activity against tomato late blight (*Phytophthora infestans*) at 300 parts per million when tested by conventional techniques.

It is to be understood that changes and variations may be made without departing from the spirit and scope of the invention as defined by the appended claims.

We claim:

1. A compound of the formula

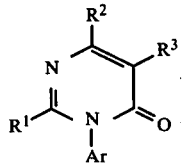

wherein $R^1$ is hydrogen, $(C_1-C_4)$ alkyl, phenyl, chlorophenyl, methylphenyl, methoxyphenyl, nitrophenyl, dichlorophenyl, benzyl or chlorobenzyl;

$R^2$ is $(C_1-C_4)$ alkyl, phenyl, chlorophenyl, methylphenyl, methoxyphenyl, nitrophenyl, dichlorophenyl, benzyl or chlorobenzyl;

$R^3$ is carboxy, carboxylate, carb $(C_1-C_{12})$ alkoxy, carbamoyl, $(C_1-C_4)$ alkyl or di $(C_1-C_4)$ alkyl carbamoyl, cyano, sulfo, sulfonate, $(C_1-C_{12})$ alkoxysulfonyl or sulfonamide;

Ar is unsubstituted phenyl, α-naphthyl or β-naphthyl or phenyl, α-naphthyl or β-naphthyl substituted with one or more substituents selected from the group consisting of $(C_1-C_4)$ alkyl, phenyl, $(C_1-C_4)$ alkoxy, phenoxy, halo, nitro, trifluoromethyl, hydroxy, $(C_2-C_6)$ alkoxyalkyl, $(C_2-C_6)$ alkoxyalkoxy, amino, $(C_1-C_4)$ alkylamino, di $(C_1-C_4)$ alkylamino, cyano, carboxy, carb $(C_1-C_4)$ alkoxy, carbamoyl, $(C_1-C_4)$ alkylcarbamoyl, di $(C_1-C_4)$ alkylcarbamoyl, sulfo, sulfonamide, $(C_1-C_4)$ alkylcarbonyl, carboxy $(C_1-C_4)$ alkyl, $(C_1-C_4)$ alkanoyloxy, halo $(C_1-C_4)$ alkyl, $(C_1-C_4)$ alkanoylamido, $(C_1-C_4)$ alkylthio, $(C_1-C_4)$ alkylsulfinyl, $(C_1-C_4)$ alkylsulfonyl and the alkali metal, alkaline earth metal, transition metal or quaternary ammonium salts or $(C_1-C_{12})$ alkyl esters thereof.

2. A compound according to claim 1 wherein $R^1$ is hydrogen or methyl;

$R^2$ is methyl; and

Ar is unsubstituted phenyl or naphthyl or phenyl or naphthyl substituted with up to three substituents selected from the group consisting of $(C_1-C_4)$ alkyl, $(C_1-C_4)$ alkoxy, halo, nitro, trihalomethyl, hydroxy, $(C_2-C_6)$ alkoxyalkyl, $(C_2-C_6)$ alkoxyalkoxy, amino, $(C_1-C_4)$ alkylamino, di $(C_1-C_4)$ alkylamino, cyano, carboxy, carb $(C_1-C_4)$ alkoxy, carbamoyl, sulfo, sulfonamide, $(C_1-C_4)$ alkylcarbonyl, $(C_1-C_4)$ alkanoyloxy, halo $(C_1-C_4)$ alkyl, $(C_1-C_4)$ alkylthio, $(C_1-C_4)$ alkylsulfinyl, $(C_1-C_4)$ alkylsulfonyl, phenyl and phenoxy.

3. A compound according to claim 2 wherein $R^3$ is carboxy or carboxylate.

4. A compound according to claim 3 wherein $R^2$ is methyl and Ar is phenyl, 1-naphthyl, 4-totyl, 4-n-butylphenyl, 2,6-xylyl, 4-methoxyphenyl, 2-chlorophenyl, 3-chlorophenyl, 4-chlorophenyl, 4-bromophenyl, 3,4-dichlorophenyl, 4-chloro-2-totyl or 4-chloro-3-totyl.

5. A compound according to claim 4 wherein $R^1$ is hydrogen and Ar is 4-chlorophenyl.

6. A compound according to claim 4 wherein $R^1$ is methyl and Ar is 4-chlorophenyl.

7. A growth regulant composition which comprises a compound according to claim 1 and an agronomically acceptable carrier.

8. A method of including male sterility in a cereal grain plant which comprises treating the plant prior to meiosis with a compound according to claim 1 in an amount sufficient to produce male sterility in the plant.

9. A method according to claim 8 wherein the compound is applied by a foliar application and wherein the plant is treated between flower initiation and meiosis.

10. A method according to claim 9 wherein the compound is applied at a rate of about 1/32 to about 20 pounds per acre.

11. A method according to claim 10 wherein the plant is wheat and the compound is applied at a rate of about ½ to about 8 pounds per acre.

12. A method according to claim 10 wherein the plant is barley and the compound is applied at a rate of about ¼ to about 8 pounds per acre.

13. A method according to claim 10 wherein the plant is rice and the compound is applied at a rate of about 1/16 to about 1 pound per acre.

14. A method according to claim 10 wherein the plant is corn and the compound is applied at a rate of about 1½ to about 12 pounds per acre.

15. A method according to claim 10 wherein the compound is 1-(4-chlorophenyl)-1,6-dihydro-4-methyl-6-oxopyrimidine-5-carboxylic acid or its sodium salt.

16. A method according to claim 10 wherein the compound is 1-(4-chlorophenyl)-1,6-dihydro-2,4-dimethyl-6-oxopyrimidine-5-carboxylic acid or its sodium salt.

17. A method of producing hybrid cereal grain seed which comprises treating a female parent of the cereal grain prior to meiosis with a compound according to claim 1 in an amount sufficient to produce male sterility in the female parent, causing the female parent to be pollinated with pollen from a male parent of the cereal grain, allowing the female parent to mature until seed formation is substantially complete, and harvesting the mature seed from the female parent.

18. A method according to claim 17 wherein the compound is applied by foliar application at a rate of about 1/32 to about 20 pounds per acre, and wherein the female parent is treated between flower initiation and meiosis.

* * * * *